United States Patent [19]

Tsolis et al.

[11] Patent Number: 4,617,184

[45] Date of Patent: Oct. 14, 1986

[54] 99M TC-1,2-DIHYDROXY-1,2-BIS(DIHYDROXY-PHOSPHINYL)ETHANE COMPLEX FOR SKELETON SCANNING

[76] Inventors: Alexandros K. Tsolis, 171 Old National Road, Arahovitika, Patra; Spyridon C. Archimandritis, 17 Hydras Street, Amarousion Attikis 15122, Athens, both of Greece

[21] Appl. No.: 676,189

[22] Filed: Nov. 29, 1984

[51] Int. Cl.[4] .................... C07F 13/00; A61K 43/00; A61N 5/12

[52] U.S. Cl. ........................................ 424/1.1; 534/14

[58] Field of Search .................. 260/429 R; 534/14

[56] References Cited

U.S. PATENT DOCUMENTS

| | | | |
|---|---|---|---|
| 3,983,227 | 9/1976 | Tofe et al. | 260/502.4 P X |
| 4,032,625 | 6/1977 | Subramanian et al. | 260/429 R |
| 4,054,645 | 10/1977 | Hill et al. | 260/429 R X |
| 4,057,615 | 11/1977 | Bardy et al. | 260/429 R X |
| 4,234,562 | 11/1980 | Tofe et al. | 260/502.4 P X |
| 4,374,821 | 2/1983 | Glavan et al. | 260/429 R X |
| 4,419,339 | 12/1983 | Neirinckx | 260/429 R X |
| 4,431,596 | 2/1984 | Tsolis et al. | 260/932 X |
| 4,497,790 | 2/1985 | Rodriguez | 260/429 R X |
| 4,512,967 | 4/1985 | Linder | 260/429 R X |
| 4,515,766 | 5/1985 | Castronovo et al. | 260/502.4 P |

*Primary Examiner*—Helen M. S. Sneed
*Attorney, Agent, or Firm*—Stiefel, Gross, Kurland & Pavane

[57] ABSTRACT

A chemical complex of Tc-99m with 1,2-dihydroxy-1,2-bis(dihydroxyphosphinyl)ethane is skeleton specific. The complex can be made by reducing pertechnetate ion and reacting the reduced technetium species with 1,2-dihydroxy-1,2-bis(dihydroxyphosphinyl)ethane.

The complex is normally used in a biologically sterile, substantially isotonic aqueous medium as a skeleton imaging agent.

7 Claims, No Drawings

99M TC-1,2-DIHYDROXY-1,2-BIS(DIHYDROXYPHOSPHINYL)ETHANE COMPLEX FOR SKELETON SCANNING

FIELD OF THE INVENTION

This invention relates to a novel chemical complex of the radioactive, metastable isotope technetium-99m (Tc-99m). A further aspect of this invention relates to a novel complex of technetium-99m wherein the complexing agent is 1,2-dihydroxy-1,2-bis(dihydroxyphosphinyl)ethane. A further aspect of this invention relates to novel processes for producing the chemical complex. A further aspect of this invention relates to a biologically sterile substantially isotonic solution containing the complex. The said solution can be preferably prepared by adding a biologically sterile substantially isotonic solution containing technetium-99m to a solid composition containing 1,2-dihydroxy-1,2-bis(dihydroxyphosphinyl)ethane, an appropriate reducing agent and a pH adjusting agent. Still another aspect of this invention relates to the use of the products and the processes of this invention for the visualization of the skeleton of mammals and the study of its biological state and/or function by the use of various known imaging and/or measuring devices and techniques, e.g. scanners and cameras, for the early diagnosis of skeleton disorders and diseases.

DESCRIPTION OF THE PRIOR ART

The art of radiochemistry has found many applications in the fields of medicine and biology. It has long been known that the introduction into an organism of compounds containing (or "labeled" with) a radioisotope can provide insight into the anatomy and physiology of the organism. These compounds, generally referred to as radiopharmaceuticals, are particularly useful in diagnostic techniques which involve studying the structure or function of various internal organs e.g. the skeleton, liver, lungs, thyroid gland etc., with radiation detection means. For diagnostic work, isotopes with a short half life and an emission spectrum rich in gamma rays (as opposed to beta particles) are preferred.

The metastable isotope Tc-99m has a 6 hour half-life and an emission spectrum, 99% gamma radiation at 140 KeV, which is extremely well suited for techniques of diagnostic nuclear medicine. Thus, Tc-99m has a high specific activity, $5.28 \times 10^9$ millicuries per gram (mCi/g). and a conveniently rapid rate of decay, whereas its daughter product, Tc-99m, has a specific activity which is almost nine orders of magnitude lower and a half life which is roughly eight orders of magnitude longer. For the organism being studied or diagnosed the slow rate of decay from the relatively stable low specific activity Tc-99 to its degradation product (ruthenium) would not normally produce any hazardous amounts of radiation, regardless of the biological means or route of elimination of a Tc-99m radiopharmaceutical. For the researcher or clinician the emission spectrum of Tc-99m can provide high levels of accuracy in radiodiagnostic measurements and calculations. In recent years Tc-99m has become readily available in hospitals through the use of selective elution from a so-called molybdenum-99 (Mo 99) generator. The isotope Mo-99 produces Tc-99m as a radioactive decay product.

Although Tc-99m compounds would appear to be ideal radiopharmaceuticals for diagnostic use, providing or selecting Tc compounds or complexes with a view toward organ specificity and tolerable levels of toxicity is a complex task. Obviously, compounds with a very low LD 50 are undesirable for human or veterinary use even in the small amounts called for diagnostic work. Compounds with insufficient in vivo stability may be poor diagnostic tools, since radioactive ions of other chemical species with insufficient or undesired organ specificity may be liberated. Stable compounds which become distributed generally throughout the organism, despite their stability, or which do not reach a desired destination in the organism are also poorly suited for many studies of organ function or structure e.g. skeleton. For these studies of organ function, compounds which are specific to an organ, but which are not excreted by it (or if excreted, are easily reabsorbed) are also poor candidates.

The problem of selecting or preparing a skeleton specific radiopharmaceutical is particularly difficult. Any radiopharmaceutical used for this purpose should ideally have 100% bone specificity. A number of chemical and biological factors must be considered and brought under control before the desired chemical purity and organ specificity of a radiopharmaceutical can be obtained. Among these factors, the structure of the technetium complexing agent is of great importance. For example some Tc compounds are easily transformed to $TcO_2$, which may lodge in the liver but may not be easily excreted causing interference problems.

Technetium-99m compounds have been used in skeleton or other organ scanning. For example Tc complexes of a number of complexing agents have been used for skeleton scanning. Representative of the literature relating to the Tc-99m complexes applied for bone imaging are the following articles and patent:

Subramanian G. et al., Radiology, 102:701 (1972), relating to 99m Tc-polyphosphate for skeletal imaging.

Perez R. et al., J. Nucl. Med., 13:788 (1972), relating to 99m-Tc-pyrophosphates for bone scanning.

Castronovo F. P. Jr., Callahan R. J., J. Nucl. Med., 13:823 (1972), relating to $^{99m}$Tc-1-hydroxy ethylidene-1,1-disodium phosphonate (HEDSPA) as a bone scanning agent.

Sabramanian G. et. al., J. Nucl. Med., 14:640 (1973), relating to $^{99m}$Tc-methylene bisphosphonate (MDP) for skeletal imaging.

Research Corporation, British Pat. No. 1,429,549 Mar. 24, 1976, relating to $^{99m}$Tc-methylene bisphosphonate for skeleton scanning.

Compared to the common transition metals, very little is known about the chemistry of technetium. Technetium belongs to Group, VII-B of the Periodic Table. Its chemistry bears a superficial resemblance to manganese but tends to be more similar to the higher member of the Group rhenium. Technetium can apparently exist in a range of oxidation states, including +7 (e.g. pertechnetate) and several lower oxidation states, some of which are difficult to characterize and/or are relatively unstable. In spectrophotometric determinations of technetium, the element has been complexed with toluene-3-4-dithiol, thioglycolic acid, and thiocyanates. See Miller et al, Anal. Chem., Page 404 (1961) and Page 1429 (October 1960), and Crouthamel. Anal. Chem. page 1756 (December 1957).

Accordingly this invention contemplates providing a complex of Tc-99m which has sufficient in vivo stability and a sufficiently high LD 50 for use in humans or animals and which preferably is:

removed from the blood or other organs or tissues and concentrated in the skeleton at a high rate;

concentrated in other organs or tissues-particularly organs or tissues in close proximity to the skeleton at a very low or negligible rate;

retained by the skeleton for a period of time long enough to permit the skeleton imaging by various devices e.g. scanners or cameras, and short enough that the radiation exposure of the organism may be negligible;

removed from the body by a means of a route passing through the kidneys; and, eliminated from the body by alternative routes (e.g. liver-gall bladder-intestines-feces) to a minor, preferably negligible, extent.

This invention further contemplates means and methods whereby a Tc-99m complex can be most efficiently produced and utilized for skeleton function studies.

The complexing agent 1,2-dihydroxy-1,2-bis(dihydroxyphosphinyl)ethane of the formula

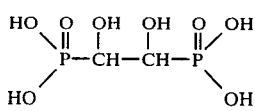

(hereinafter referred to as DHPE), which is used for the production of the Tc-99m complex of this invention has been produced by a method covered by the U.S. Pat. No. 4,431,596 Feb. 14, 1984 of Alexandros K. Tsolis and Ioannis A. Mikroyannidis. A divisional patent for DHPE is pending.

BRIEF SUMMARY OF THE INVENTION

Briefly, this invention involves reducing an appropriate amount of radioactive pertechnetate ion ($^{99m}TcO_4^-$) until a major amount of the pertechnetate ion has been reduced to a technetium species, having an oxidation state greater than 0 but less than $+7$ and then reacting this technetium species with an excess of the complexing agent DHPE.

The resulting Tc-99m complex is suitable for injection into the blood stream of a mammal when dissolved in a biologically sterile aqueous medium substantially isotonic with mammalian body fluids. The reduction step can be carried out electrochemically in a cell equipped with metal electrodes such as tin or zirconium. Preferably, however reduction is achieved chemically through the use of a reducing agent such as a tin (II) salt, preferably in the presence of the complexing agent DHPE in an aqueous medium. The preferred range of pH is between 5 and 7.

A meaningful picture of skeleton function is obtained by measuring the radioactivity emitted from the bones of the organism or patient being studied. It will generally not be necessary to monitor the radioactivity for more than about 24 hours after the injection, and 12 hours of monitoring can be sufficient. The product of the present invention has the desired bone specificity which leads to a very good skeleton visualization.

DETAILED DESCRIPTION OF THE INVENTION

As pointed out previously, the complexing agent DHPE elected for use in this invention is capable of providing a Tc-99m bone specific imaging compound which is suitable for inclusion in injectable media substantially isotonic with mammalian body fluids, which in vivo is rapidly removed from the blood or other tissues by the skeleton. The term "substantially isotonic with mammalian body fluids", as used herein, denotes the situation obtained when the osmotic pressure exerted by the solution in question is sufficiently similar, as compared to a body fluid such as blood, so that no dangerous hypo- or hypertonic condition results in the patient or test animal when 0.1 ml (in the case of a mouse) or up to 10 ml (in the case of a human) of the solution is injected into the patient's or animal's bloodstream.

The exact mechanism by which the complexing agent DHPE used in this invention becomes chemically linked to technetium is difficult to determine. It appears that the Tc-99m should be present primarily in an oxidation state of at least about $+3$ but not more than $+6$. This oxidation state can be conveniently obtained by reducing 99m-pertechnetate, a relatively stable $+7$ technetium species. It appears also that responsible for the efficient technetium complexing are the ionizable P-OH groups of DHPE in combination with its C—OH groups. This is evidenced by our experimental finding that tetraalkylesters of DHPE did not form stable technetium complexes. The preferred range of pH is between 5 and 7.

The amount of Tc-99m needed to produce an amount of radiopharmaceutical suitable for most diagnostic or research uses is extremely small and is generally in the range of about 0.5 millicuries per milliliter (mCi/ml) of 99m pertechnetate solution up to about 10 mCi per ml of such solution. Only about $0.03 \times 10^{-10}$ grams of 99m-pertechnetate dissolved in a milliliter of aqueous medium (e.g. isotonic saline) is needed to provide 0.01 mCi/ml, and less than $100 \times 10^{-10}$ gram of 99m-pertechnetate per milliliter of solution provides enough radioactivity for most uses. Due to the short half-life of the Tc-99m, it is preferred to prepare small batches of 99m-pertechnetate solution for immediate use. Batches as small as 0.1 ml can be adequate for animal studies (e.g. for injection in mice) and batches as large as 10 ml are convenient for one or more injections in one or a group of human patients.

In any event it would be a rare situation that required more than about $100 \times 10^{-10}$ gram (i.e. about $10^{-10}$ gram-atoms) of Tc-99m as pertechnetate ion to produce a few ml of radiopharmaceutical, regardless of stoichiometry of the Tc complex. It is preferred to provide enough complexing agent (ordinarily at least $5 \times 10^{-9}$ moles per milliliter of reaction mixture) to have an excess over stoichiometry with respect to the Tc-99m in the reaction mixture. A large excess of complexing agent (e.g. 0.5–500 nmol of complexing agent permCi of reaction mixture) can be desirable.

The Tc-99m used in this invention is obtainable from a Mo-99 generator in the conventional manner. Eluting or "milking" the generator with an aqueous medium will provide the 99m-pertechnetate solution in the form of $M^{+x}(^{99m}TcO_4^-)_x$, where $M^{+x}$ is a pharmaceutically acceptable cation such as a proton, an alkali metal ion, an ammonium ion, or the like, and x is a positive integer less than 4. Typically, the aqueous elution medium is a saline solution, which provides sodium 99m-pertechnetate.

Tc-99m used in this invention is also obtained by methylethylketone extraction of a 6N sodium hydroxide solution of $^{99}$MoO$_3$. The methylethylketone phase is freed from water traces by passing through a short column of acid grade alumina, evaporated to dryness and the sodium pertechnetate residue is dissolved in saline. Tc-99m obtained in this way is usually called "instant technetium".

The pertechnetate ion can be reduced chemically or electrolytically to a lower oxidation state of technetium, preferably by reaction with an oxidizable low valence metal salt such as a tin (II) salt (e.g. SnCl$_2$), an iron (II) salt (e.g. a ferrous salt/ascorbic acid medium), a Cu(I)/-Cu(II) couple, a combination thereof, or other chemical reducing agents such as mercaptans, metal hydrides, thiosulfates, hypophosphites, bromides, iodides, etc. The reduction of the pertechnetate ion can be preferably carried out in the presence of the complexing agent DHPE.

A suitable means for providing the reducing agent, the complexing agent and the pH adjusting agent is to preformulate a radiopharmaceutical kit for use with the Mo-99 generator eluate or with "instant technetium". For example 0.1, preferably at least 0.5 to 1 mL, of an aqueous solution containing about 0.5–500 nmol/mL of DHPE, a suitable amount e.g. 1 to 660 nmol/mL of reducing agent, and a suitable amount of an agent, e.g. CH$_3$COONa capable of adjusting the pH of the solution to between 5.00 and 7.00, preferably at 5.50, can be hermetically and aseptically sealed in a vial. A preservative such as benzyl alcohol is optionally included in the contents of the vial. The solution in the vial is preferably substantially isotonic with mammalian body fluids e.g. human blood.

The contents of the vial can be combined with the pertechnetate-containing, substantially isotonic eluate to achieve the reduction and Tc-complex formation, and the resulting radiopharmaceutical can then be injected into the blood stream of the patient or test animal. Radioactivity measurements are made in the conventional manner for a period from the time of injection until about 24 hours afterwards, depending on the nature of the study or diagnosis. Most studies call for at least one half hour of post injection radioactive measurements. These measurements can be corrected for decay in the usual manner and studied with a view toward obtaining a picture of the skeleton.

A most efficient and particularly suitable means for producing the radiopharmaceutical is to preformulate a kit obtainable by freeze drying the above solution containing the complexing agent, the reducing agent and the pH adjusting agent for utilization with the Mo-99 generator eluate or with "instant technetium".

The radiopharmaceutical can also be produced by electrochemical reduction of a $^{99m}$TcO$_4^-$ saline solution by means of a cell equipped with, for example, tin electrodes. The cell contains 0.1, preferably at least 0.5 to 1 mL, of an aqueous solution containing about 0.5 to 500 nmol/mL of DHPE as well as a suitable amount of an agent, e.g. CH$_3$COONa, capable to adjust the pH of the solution to between 2.50 and 7.00 preferably to 5.50. A volume of 1-2 mL of $^{99m}$TcO$_4^-$ saline solution is added to the cell and an electrical charge of $5 \times 10^{-2}$ coulombs (20 sec $\times$ 2.5 mA) passes through to provide the $^{99m}$T-DHPE complex in high radiochemical purity.

The determination of the acute and chronic toxicity of DHPE in rodents showed no deaths or adverse effects for injected doses in the range of 5 to 250 mg per kg of body weight. The amount of complexing agent required to be injected into a test animal or human patient for a satisfactory skeleton scintigraphy is three orders of magnitude smaller than the highest tested dose.

The radiochemical purity of the radiopharmaceutical $^{99m}$Tc-DHPE produced according to this invention can be easily determined by thin layer or paper chromatography and radiation monitoring since TcO$_4^-$ and its reduced-and-complexed form have distinctly different $R_f$ values if the chromatogram is developed with properly selected solvents.

The distinct $R_f$ value of the novel $^{99m}$Tc-DHPE complex produced according to this invention can reliably characterize this compound so that it is distinguished from its precursor. Since only minute amounts of complexes of $^{99m}$Tc can be produced, analysis of the complex by any method other than paper or thin layer chromatography is extremely difficult at best. To reproducibly determine the Rf values, paper and thin layer chromatograms can be made from appropriate solutions and standanized chromatogram sheets. Reproducible results have been obtained with Whatman No 1 paper sheets or with 100 micron thick silica gel G glass plates and with the commercially available silica gel thin layer sheets, Gelman-ITLC-SG. Several paper or thin layer chromatograms can be made and averaged as a double check on the experimental error inherent in the $R_f$, but generally this error is very small. The chromatograms are developed with polar solvent systems such as methanol:water 85:15 v/v and 85% aqueous phosphonic acid:water 15:85 v/v as described subsequently.

The radiopharmaceutical $^{99m}$Tc-DHPE of this invention, when compared to the other known skeleton imaging radiopharmaceuticals, offers the following advantages:

It is easily and efficiently produced according to the method of this invention, in a better than 98% radiochemical purity, from the very low toxicity and efficient Tc-99m complexing agent, DHPE, preferably from a freeze dried kit, which is stable for at least six months, when stored at 2°–8° C., and which shows high flexibility with respect to the volume and the radioactive concentration of the $^{99m}$Tc saline solution utilized for the labeling. It has an appropriate in vivo stability. It is removed from the blood or other organs and tissues and concentrated in the skeleton at a higher rate.

It is concentrated to other organs or tissues at a very low in negligible rate.

The result of the above in vivo performance is a high quality skeleton visualization, after a short post injection period of time, which may be utilized for skeleton structure and function studies.

The invention is illustrated by the non-limiting Examples which follow.

EXAMPLE 1

$^{99m}$Tc-1,2-Dihydroxy-1,2-bis(dihydroxyphosphinyl)ethane Complex Preparation from a Freeze Dried Kit and Distribution in Rats Twenty five milliliters of a sterile aqueous solution of 55.5 mg of DHPE were mixed with 12.5 mL of a freshly prepared sterile aqueous solution containing 0.1 mg of SnCl$_2$ per milliliter and with 12.5 mL of a sterile aqueous solution of sodium acetate 10% W/V. Portions of 2 mL each of the resulting solution were transferred through a Millipore filter of 0.22 micron pore size into pharmaceutical vials. The vials were freeze dried for 24 hours and were sealed in vacuum. Four milliliters of saline solution of Na+$^{99m}$TcO$_4^-$ (20 millicuries Tc-99m) were added to each vial. The vial was vigorously shaken, and then allowed to stand for five minutes at normal ambient temperature. Analysis with paper chromatography on two Whatman No 1 paper sheets of dimensions 2×30 cm using methanol:water 85:15 v/v and 85% aqueous phosphoric acid:water 15:85 v/v showed radiochemical purity of the complex of 98%.

Two hundred fifty microliters of the above solution of the radiopharmaceutical $^{99m}$Tc-DHPE were injected i.v. (intravenously) in the tail vein of each of six Hooded strain, closed colony, random breeding rats. The rats were sacrificed at the following time periods 1 hr, 2 hr, 4 hr, 6 hr, 12 hr, and 24 hrs. The organs of each rat were isolated and the distribution of Tc-99m determined by assay with a single channel analyzer equipped with a well type NaI(Tl) scintillation detector. The results of this study are shown in Table I.

Developed chromatograms:
When developed with solvent (1), $R_f=0$ for the $^{99m}$Tc-DHPE complex and the reduced-hydrolyzed noncomplexed technetium (TcO$_2$ or TcO(OH)$_2$), but the $R_f$ was about 0.65 for unreacted pertechnetate.
When developed with solvent (2), $R_f=0$ for the reduced hydrolyzed noncomplexed technetium, $R_f=0.7$ for the unreacted pertechnetate and $R_f=1.0$ for the $^{99m}$Tc-DHPE complex.

EXAMPLE 2

$^{99m}$Tc-1,2-Dihydroxy-1,2-bis(dihydroxyphosphinyl)ethane Complex Preparation from a Solution Kit and Gamma Camera Monitoring in Anesthetized Rabbit Two milliliters of a sterile saline solution of Na+$^{99m}$TcO$_4^-$ (IO millicuries Tc-99m) were added to a pharmaceutical vial containing 2 mL of a sterile aqueous solution containing 2.2 mg of DHPE, 50μg of

TABLE I

| ORGAN | ORGAN DISTRIBUTION OF $^{99m}$Tc-DHPE IN RATS* Dose per Organ | | | | | |
|---|---|---|---|---|---|---|
| | 1 hr | 2 hr | 4 hr | 6 hr | 12 hr | 24 hr |
| BLOOD | 0.742 ± 0.384 | 0.895 ± 0.515 | 0.643 ± 0.414 | 0.322 ± 0.067 | 0.312 ± 0.209 | 0.104 ± 0.015 |
| SPLEEN | 0.020 ± 0.007 | 0.026 ± 0.007 | 0.020 ± 0.003 | 0.022 ± 0.007 | 0.008 ± 0.002 | 0.010 ± 0.004 |
| STOMACH | 0.288 ± 0.137 | 0.388 ± 0.176 | 0.226 ± 0.243 | 0.152 ± 0.148 | 0.082 ± 0.023 | 0.040 ± 0.029 |
| LIVER | 0.095 ± 0.018 | 0.184 ± 0.049 | 0.187 ± 0.032 | 0.168 ± 0.044 | 0.131 ± 0.022 | 0.134 ± 0.030 |
| LUNGS | 0.104 ± 0.033 | 0.149 ± 0.105 | 0.121 ± 0.029 | 0.032 ± 0.007 | 0.022 ± 0.015 | 0.044 ± 0.024 |
| HEART | 0.022 ± 0.008 | 0.026 ± 0.012 | 0.018 ± 0.008 | 0.015 ± 0.004 | 0.011 ± 0.005 | 0.006 ± 0.001 |
| KIDNEYS | 1.523 ± 0.371 | 1.782 ± 0.365 | 1.441 ± 0.277 | 2.716 ± 0.365 | 3.018 ± 0.825 | 1.187 ± 0.119 |
| BONE | 44.426 ± 2.556 | 45.722 ± 3.411 | 53.447 ± 2.828 | 47.673 ± 6.612 | 42.362 ± 4.449 | 43.317 ± 2.825 |
| MUSCLE | 1.138 ± 0.511 | 2.371 ± 1.206 | 2.193 ± 0.974 | 4.216 ± 2.815 | 2.139 ± 0.389 | 2.699 ± 1.989 |
| ADRENALS | 0.006 ± 0.006 | 0.007 ± 0.005 | 0.003 ± 0.001 | 0.003 ± 0.001 | 0.001 ± 0.000 | 0.001 ± 0.000 |
| LARGE INTESTINE | 1.548 ± 1.380 | 2.210 ± 1.789 | 2.906 ± 3.009 | 3.209 ± 0.684 | 0.648 ± 0.615 | 0.415 ± 0.448 |
| SMALL INTESTINE | 0.963 ± 0.868 | 1.963 ± 2.085 | 1.009 ± 1.243 | 0.495 ± 0.205 | 0.318 ± 0.113 | 0.091 ± 0.033 |
| FECES | 0.034 ± 0.054 | 0.053 ± 0.088 | 0.394 ± 0.343 | 0.570 ± 0.205 | 0.848 ± 0.601 | 3.149 ± 1.799 |
| URINE | 28.584 ± 5.562 | 28.295 ± 1.829 | 31.469 ± 4.991 | 24.033 ± 5.995 | 6.519 ± 3.702 | 8.600 ± 3.643 |

*Average value for six animals each. ± the standard deviation

The experimental error in the distribution vs. time data for the $^{99m}$Tc-DHPE complex was minimized by averaging six runs under identical conditions, always with the Hooded strain rats. The effect of organ geometry on radioactivity counting efficiency was taken into account. Corrections were also made so that, upon extrapolation back to time zero, the summation of activity in the organs was equal to the injected activity (i.e. by comparison to standards).

The freeze dried kit utilized for the production of the $^{99m}$Tc-DHPE complex by following the previously outlined procedure contained the following optimized amounts of the reactants:

| DHPE | 2.2 mg |
|---|---|
| SnCl$_2$ | 50 μg |
| CH$_3$COONa | 50 mg |
| $^{99m}$TcO$_4^-$ solution | 4.0 mL (20 mCi$^{99m}$Tc) |

These studies clearly show the fast removal of the $^{99m}$Tc-DHPE complex from the blood, its fast and high concentration to the skeleton, in comparison to other organs or tissues and its excretion mainly via the kidneys to urine.

Paper chromatographic analysis of the $^{99m}$Tc-DHPE complex was carried out as follows
Chromatogram:
Whatman No 1 paper sheets, 2×30 cm
Solvent systems:
1. methanol:water 85:15 v/v
2. 85% aqueous phosphoric acid:water 15:85 v/v SnCl$_2$ and 50 mg of CH$_3$COONa. The vial was vigorously shaken, then allowed to stand for five minutes at room temperature. Paper chromatography of the solution was run according to the method outlined in Example 1 and only 2% unreacted pertechnetate was found.

Bone imaging was carried out by intravenous injection of 0.5 milliliters of this solution into the ear vein of an anesthetized rabbit positioned under a gamma camera. The output of the gamma camera was attached to a computer so the data could later be played back displayed, photographed and analyzed. After a post injection period of thirty minutes, the skeleton was clearly visualized. As time passed the quality of the images improved. Excellent images of the skeleton were obtained after a post injection time of 1 to 2.5 hrs. The obtained data showed a fast removal of the radiopharmaceutical from the blood. Less than 30% of the initial radioactivity in the blood was detected in the blood 30 minutes after injection.

EXAMPLE 3

$^{99m}$Tc-1,2-Dihydroxy-1,2-bis(dihydroxyphosphinyl)ethane Complex Preparation by electrochemical Reduction and Distribution in Rats Four milliliters of a sterile aqueous solution containing 1.5 mg of DHPE, 20 mg of CH$_3$COONa and 10 mCi of Na+$^{99m}$TcO$_4^-$ were added to a sterile cell equipped with tin electrodes. An electrical charge of 5×10$^{-2}$ coulombs (20 sec×2.5 mA) was passed through to produce the $^{99m}$Tc-DHPE complex. Paper chromatography of the solution was run according to the method outlined in Example 1. The determined radiochemical purity of the $^{99m}$Tc-DHPE compound was 98%. The complex was assayed by intravenous injections into the tail veins of Hooded strain rats as in Example 1, the animals being sacrificed at 1, 2, 4, 6, 12, and 24 hours. The assay indicated a rapid skeleton uptake of the complex and its excretion mainly to the urine. Uptake by other organs did not detract significantly from bone specificity.

What is claimed is:

1. A process for making a $^{99m}$Tc-1,2-dihydroxy-1,2-bis(dihydroxyphosphinyl)ethane complex which is bone specific in vivo comprising the steps of:
   a. reducing a solution comprising at least 0.5 but less than 10 millicuries per milliliter of 99m-pertechnetate ion until more than 95 mol % of said 99m-pertechnetate ion has been reduced to a 99m-technetium species having an oxidation state greater than zero but less than +7; and
   b. reacting said 99m-technetium species with an excess of the complexing agent 1,2-dihydroxy-1,2-bis(dihydroxyphosphinyl)ethane, regardless of the stoichiometry of the resulting product, at a pH in the range of 5 to 7.

2. A process according to claim 1 wherein the reduction is carried out in the presence of the complexing agent 1,2-dihydroxy-1,2-bis(dihydroxyphosphinyl)ethane at a pH in the range of 5 to 7.

3. A process according to claim 1 wherein the pertechnetate ion solution is mixed with a mixture of excess 1,2-dihydroxy-1,2-bis(dihydroxyphosphinyl)ethane, excess reducing agent and the appropriate quantity of an agent for the adjustment of the pH to between 5 and 7.

4. A process according to claim 1 wherein said reduction step is carried through the use of a reducing agent selected from the group consisting of a tin (II) salt, an iron (II) salt, and a Cu(I)/Cu(II) couple.

5. A process according to claim 1 wherein said reduction step is carried out electrochemically through the use of electrodes selected from the group consisting of tin and zirconium.

6. A skeleton specific $^{99m}$Tc-1,2-dihydroxy-1,2-bis(dihydroxyphosphinyl)ethane complex, said complex being characterized by the following $R_f$ values determined by paper chromatography on Whatman No 1 paper sheets:
   $R_f=0$, when said chromatogram developed with a solvent system consisting of methanol:water in the volume/volume ratio of 85:15.
   $R_f=1$, when said chromatogram developed with a solvent system consisting of 85% aqueous phosphoric acid:water in the volume/volume ratio of 15:85.

7. The method of claim 8, wherein the complex is characterized by the following $R_f$ values determined by paper chromatography on Whatman No 1 paper sheets:
   $R_f=0$, when said chromatogram is developed with a solvent system consisting of methanol:water in the volume/volume ratio of 85:15, and
   $R_f=1$, when said chromatogram is developed with a solvent system consisting of 85% aqueous phosphoric acid:water in the volume/volume of ratio of 15:85.

* * * * *

UNITED STATES PATENT AND TRADEMARK OFFICE
CERTIFICATE OF CORRECTION

PATENT NO. : 4,617,184
DATED : October 14, 1986
INVENTOR(S) : ALEXANDROS K. TSOLIS It is certified that error appears in the above—identified patent and that said Letters Patent is hereby corrected as shown below:

```
Col. 2, line 41:   delete "-" between "99m" and "Tc"
Col. 2, line 49:   "Pat." should read --Patent--
Col. 2, line 54:   After "group" delete ","
Col. 2, line 57:   After "group" insert --,--
Col. 3, line 5:    "-" should read --,--
Col. 4, line 18:   After "least" delete "about"
Col. 5, line 59:   "2.50" should read --5.00--
Col. 6, line 48:   "to" should read --in--
Col. 6, line 49:   "in" should read --to--
Col. 6, line 60:   After "Rat" insert --.--
Col. 8, line 15:   After "Rabbit" insert --.--
Col. 8, line 48:   After "back" insert --,--
Col. 8, line 63:   After "Rats" insert --.--

Col. 10, line 23:  Change "8," to --6,--
```

Signed and Sealed this

Eighteenth Day of December, 1990

*Attest:*

HARRY F. MANBECK, JR.

*Attesting Officer*  *Commissioner of Patents and Trademarks*